United States Patent
Sakamoto

(10) Patent No.: US 10,729,431 B2
(45) Date of Patent: Aug. 4, 2020

(54) SUTURE DEVICE

(71) Applicant: OLYMPUS CORPORATION, Tokyo (JP)

(72) Inventor: Tetsuyuki Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 216 days.

(21) Appl. No.: 15/802,720

(22) Filed: Nov. 3, 2017

(65) Prior Publication Data

US 2018/0064436 A1 Mar. 8, 2018

Related U.S. Application Data

(63) Continuation of application No. PCT/JP2016/061200, filed on Apr. 6, 2016.

(30) Foreign Application Priority Data

Jul. 29, 2015 (JP) .................. 2015-149589

(51) Int. Cl.
*A61B 17/062* (2006.01)
*A61B 17/04* (2006.01)
*A61B 17/00* (2006.01)

(52) U.S. Cl.
CPC ........ *A61B 17/062* (2013.01); *A61B 17/0469* (2013.01); *A61B 17/0491* (2013.01);
(Continued)

(58) Field of Classification Search
CPC ............ A61B 17/0469; A61B 17/0491; A61B 17/062; A61B 17/0625; A61B 17/28;
(Continued)

(56) References Cited

U.S. PATENT DOCUMENTS 1,933,024 A * 10/1933 Nagelmann ............ A61B 17/04
606/145
2004/0260314 A1 12/2004 Lizardi et al.
(Continued)

FOREIGN PATENT DOCUMENTS

EP 1 498 075 A1 1/2005
EP 2108319 A1 10/2009
(Continued)

OTHER PUBLICATIONS

Extended Supplementary European Search Report dated Mar. 22, 2019 in European Patent Application No. 16 83 0107.5.
(Continued)

*Primary Examiner* — Darwin P Erezo
*Assistant Examiner* — Christian D Knauss
(74) *Attorney, Agent, or Firm* — Scully, Scott, Murphy & Presser, P.C.

(57) ABSTRACT

A suture device including: an elongated shaft member extending along a longitudinal axis; a pair of gripping members provided at a distal end of the elongated shaft member in a pivotable manner about a pivot orthogonal to the longitudinal axis so as to be opened and closed relative to each other; and a passing mechanism which passes a suture needle between the gripping members, in which the gripping members include: fitting hole portions which are formed along an opening-closing direction of the gripping members, and to which the suture needle is detachably fitted; and contact portions which are brought into contact with front and back surfaces of a suture object in a course of a closing action of the gripping members so as to suppress a movement of the suture object along the front surface of the suture object.

3 Claims, 14 Drawing Sheets

(52) U.S. Cl.
CPC .. *A61B 17/0625* (2013.01); *A61B 2017/0034* (2013.01); *A61B 2017/00862* (2013.01)

(58) Field of Classification Search
CPC ... A61B 17/2812; A61B 17/282; A61B 17/29; A61B 2017/2926; A61B 2017/2945; A61B 10/06; A61B 2017/2808; A61B 2017/2825

See application file for complete search history.

(56) References Cited

U.S. PATENT DOCUMENTS

| | | |
|---|---|---|
| 2007/0123914 A1 | 5/2007 | Lizardi et al. |
| 2007/0185487 A1 | 8/2007 | Hafner |
| 2009/0204127 A1* | 8/2009 | Sinnott .............. A61B 17/0469 606/139 |
| 2009/0259233 A1 | 10/2009 | Bogart et al. |
| 2010/0010512 A1 | 1/2010 | Taylor et al. |
| 2010/0030028 A1 | 2/2010 | Cabrera et al. |
| 2010/0030238 A1 | 2/2010 | Viola et al. |
| 2010/0030239 A1 | 2/2010 | Viola et al. |
| 2010/0076460 A1 | 3/2010 | Taylor et al. |
| 2010/0076461 A1 | 3/2010 | Viola et al. |
| 2010/0094083 A1 | 4/2010 | Taylor et al. |
| 2010/0217282 A1 | 8/2010 | Cabrera et al. |
| 2010/0228270 A1 | 9/2010 | Bogart et al. |
| 2010/0274265 A1 | 10/2010 | Wingardner et al. |
| 2012/0277768 A1 | 11/2012 | Viola et al. |
| 2012/0277769 A1 | 11/2012 | Cabrera et al. |
| 2013/0035703 A1 | 2/2013 | Taylor et al. |
| 2013/0110136 A1 | 5/2013 | Viola et al. |
| 2013/0123815 A1 | 5/2013 | Wingardner, III et al. |
| 2013/0261644 A1 | 10/2013 | Taylor et al. |
| 2013/0317291 A1* | 11/2013 | Yamamoto ......... A61B 17/0487 600/104 |
| 2013/0317525 A1 | 11/2013 | Wingardner, III et al. |
| 2015/0230790 A1 | 8/2015 | Hashimoto |
| 2016/0174967 A1 | 6/2016 | Taylor et al. |

FOREIGN PATENT DOCUMENTS

| | | |
|---|---|---|
| EP | 2374416 A2 | 10/2011 |
| EP | 2494929 A1 | 9/2012 |
| EP | 2494930 A1 | 9/2012 |
| EP | 2 889 008 A1 | 7/2015 |
| JP | 2008508964 A | 3/2008 |
| JP | 2010505525 A | 2/2010 |
| JP | 2014158657 A | 9/2014 |
| WO | 2008045394 A2 | 4/2008 |
| WO | 2013008817 A1 | 1/2013 |

OTHER PUBLICATIONS

International Search Report dated Jun. 28, 2016 issued in PCT/JP2016/061200.

* cited by examiner

SUTURE DEVICE

CROSS-REFERENCE TO RELATED APPLICATIONS

This is a Continuation Application of International Application No. PCT/JP2016/061200 filed on Apr. 6, 2016, which claims priority to Japanese Application No. 2015-149589 filed on Jul. 29, 2015. The contents of International Application No. PCT/JP2016/061200 and Japanese Application No. 2015-149589 are hereby incorporated herein by reference in its entirety.

TECHNICAL FIELD

The present invention relates to a medical suture device.

BACKGROUND ART

Conventionally, suture devices for suturing tissue or the like in a body have been known (see PTL 1 and PTL 2).

A suture device includes two openable/closable gripping members at a distal end of an elongated shaft member that is inserted into the body of a patient. The gripping members are provided with a passing mechanism which passes a suture needle. A suture object is sandwiched by two gripping members in a state where the suture needle to which a suture thread is attached is held by one of the gripping members. With such an operation, the suture needle is made to penetrate the suture object. By alternately passing the suture needle by means of the passing mechanism between the two gripping members, the suture object is sutured.

In suture devices disclosed in PTL 1 and PTL 2, a pointed end portion of a suture needle held by one of the gripping member is pressed against a suture object disposed between the pointed end portion of the suture needle and the other gripping member. In pushing the suture needle into a needle receiving hole formed in the other gripping member, the suture object is pierced by the pointed end portion. In such a manner, the suture needle is made to penetrate the suture object.

CITATION LIST

Patent Literature

{PTL 1}
Japanese Translation of PCT International Application, Publication No. 2010-505525
{PTL 2}
Japanese Unexamined Patent Application, Publication No. 2014-158657

SUMMARY OF INVENTION

According to one aspect of the present invention, there is provided a suture device which includes: an elongated shaft member extending along a longitudinal axis; a pair of two gripping members, the gripping members being provided at a distal end of the elongated shaft member in a pivotable manner about a pivot orthogonal to the longitudinal axis so as to be opened and closed relative to each other; and a passing mechanism configured to pass a suture needle between the gripping members, the suture needle to which a suture thread is attached and which has a pointed end portion, wherein each of the gripping members includes: a fitting hole portions which is formed along an opening and closing direction of the gripping members, and to which the suture needle is detachably fitted; and a contact portion which is brought into contact with either of front and back surfaces of a suture object in a course of a closing action of the pair of the gripping members so as to suppress a movement of the suture object in a direction along the surface of the suture object.

DESCRIPTION OF EMBODIMENTS

A suture device 1 according to one embodiment of the present invention is described hereinafter with reference to drawings.

Figure 1:
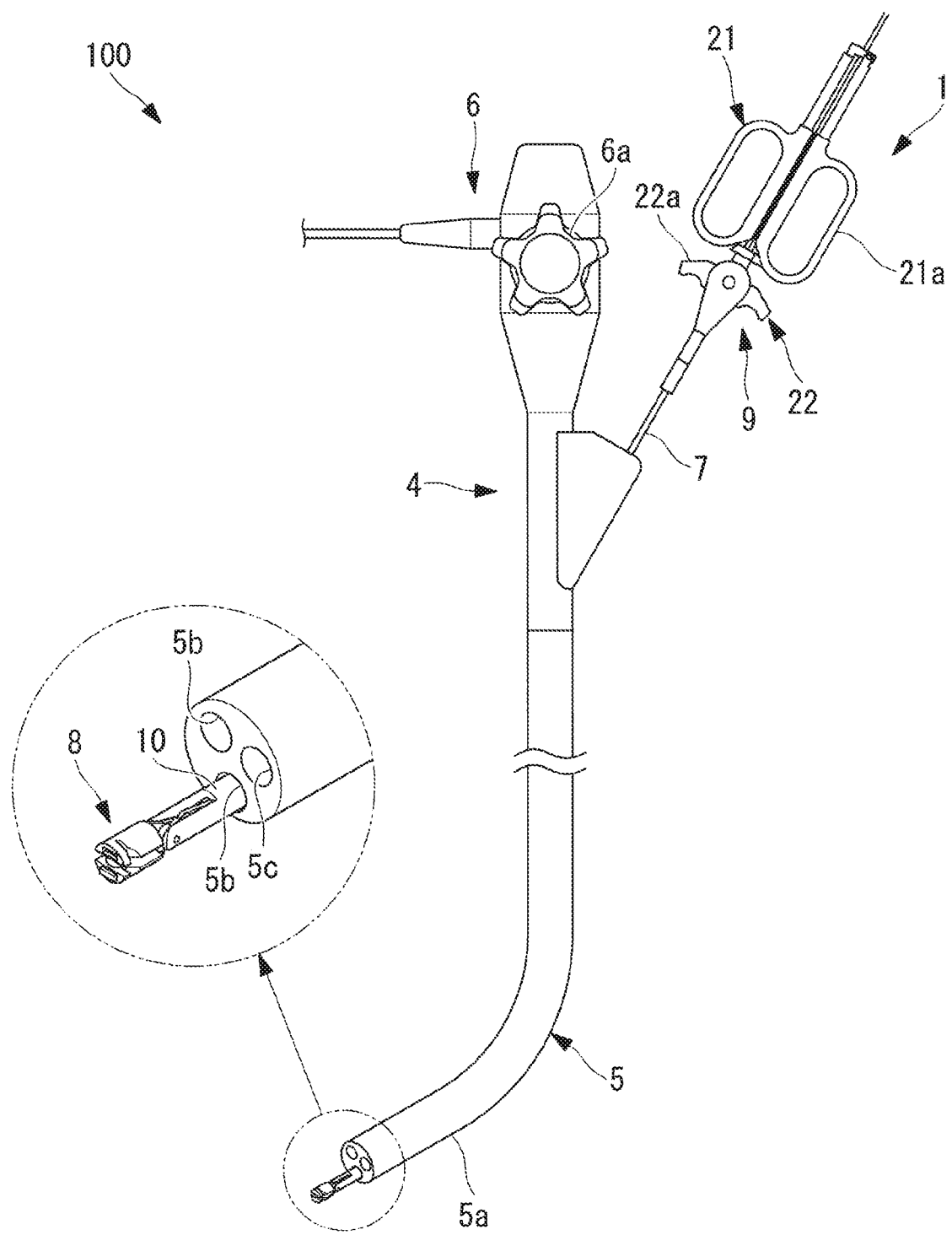
FIG. 1 is an overall constitutional view showing a suture system which includes a suture device according to one embodiment of the present invention.

A suture system 100 in which the suture device 1 according to this embodiment is used is shown in FIG. 1.

Figure 3:
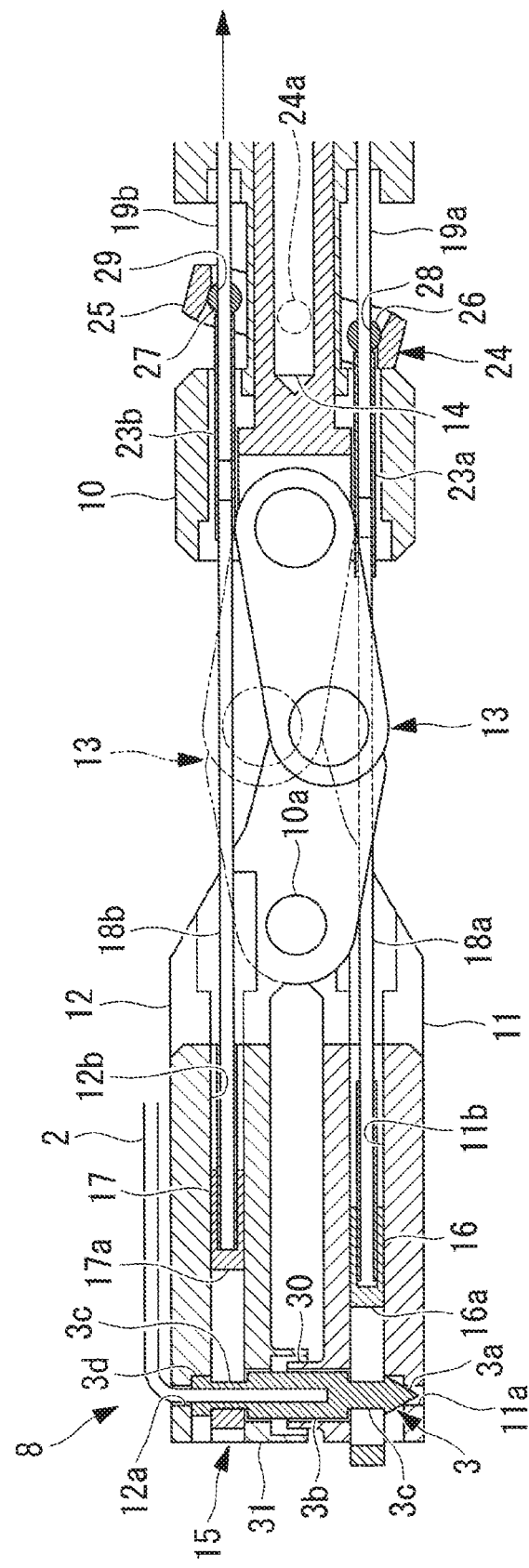
FIG. 3 is a longitudinal cross-sectional view of the treatment portion shown in FIG. 2.
Figure 4A:
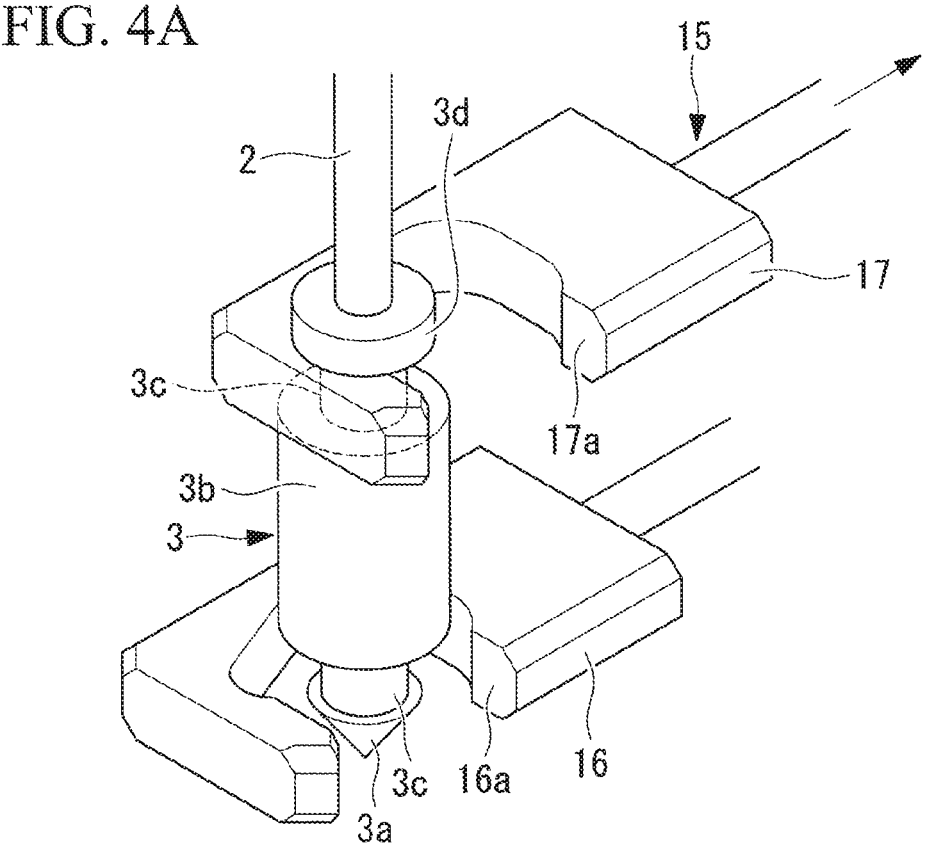
FIG. 4A is a view showing a relationship between holding members and a suture needle of the treatment portion shown in FIG. 2, and is also a perspective view showing a state where the holding member on the flange portion side holds the suture needle.
Figure 4B:
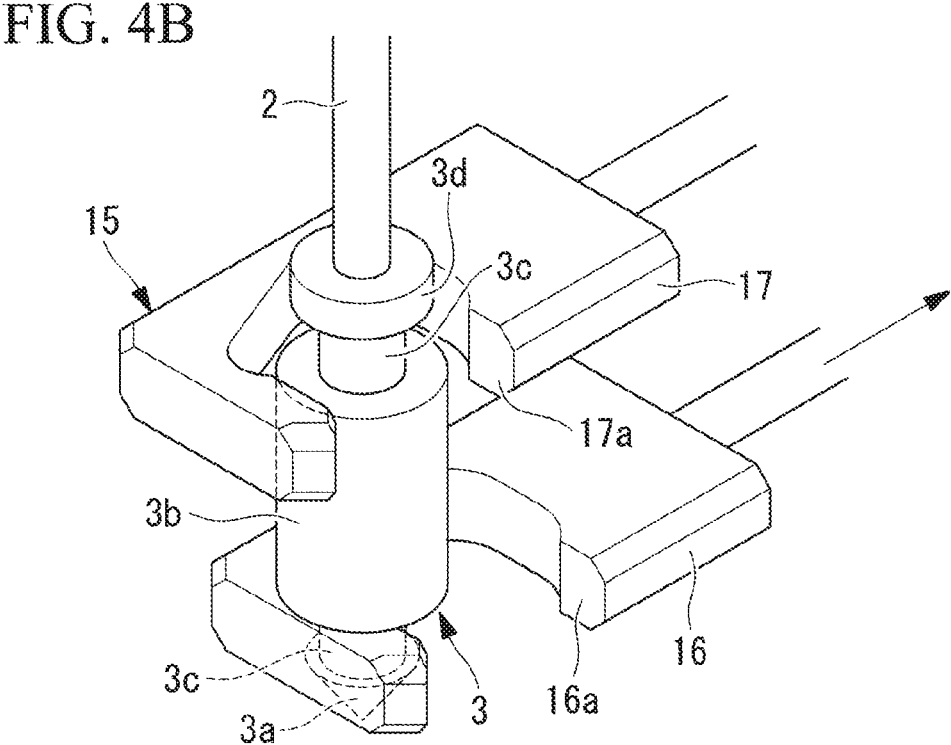
FIG. 4B is a view showing a relationship between the holding members and the suture needle of the treatment portion shown in FIG. 2, and is also a perspective view showing a state where the holding member on the pointed end portion side holds the suture needle.

As shown in FIGS. 3 to 4B, the suture system 100 is a system which sutures tissue A using a suture needle 3 where a suture thread 2 is fixed to one end of the suture needle 3, and a pointed end portion 3a is formed on the other end of the suture needle 3. As shown in FIG. 1, the suture system 100 includes an endoscope 4 and the suture device 1 according to this embodiment.

The endoscope 4 is formed of a known endoscope, and includes a manipulation portion 6, which is manipulated by an operator, on the proximal end side of an elongated flexible insertion portion 5. A bending portion 5a is formed on a distal end portion of the insertion portion 5, and the bending portion 5a is bendable by a manipulation of a knob 6a of the manipulation portion 6.

In the insertion portion 5 of the endoscope 4, two channels 5b penetrating in the longitudinal direction and opening at the distal end surface are provided. In the drawing, reference symbol "5c" denotes an observation optical system. The number of channels 5b may be one or three or more.

The suture device 1 according to this embodiment includes: a long flexible tubular elongated shaft member 7 having an outer diameter size which allows the elongated shaft member 7 to be inserted into the channel 5b; a treatment portion 8 provided at a distal end of the elongated shaft member 7; and a manipulation portion 9 provided at a proximal end of the elongated shaft member 7.

Figure 2:
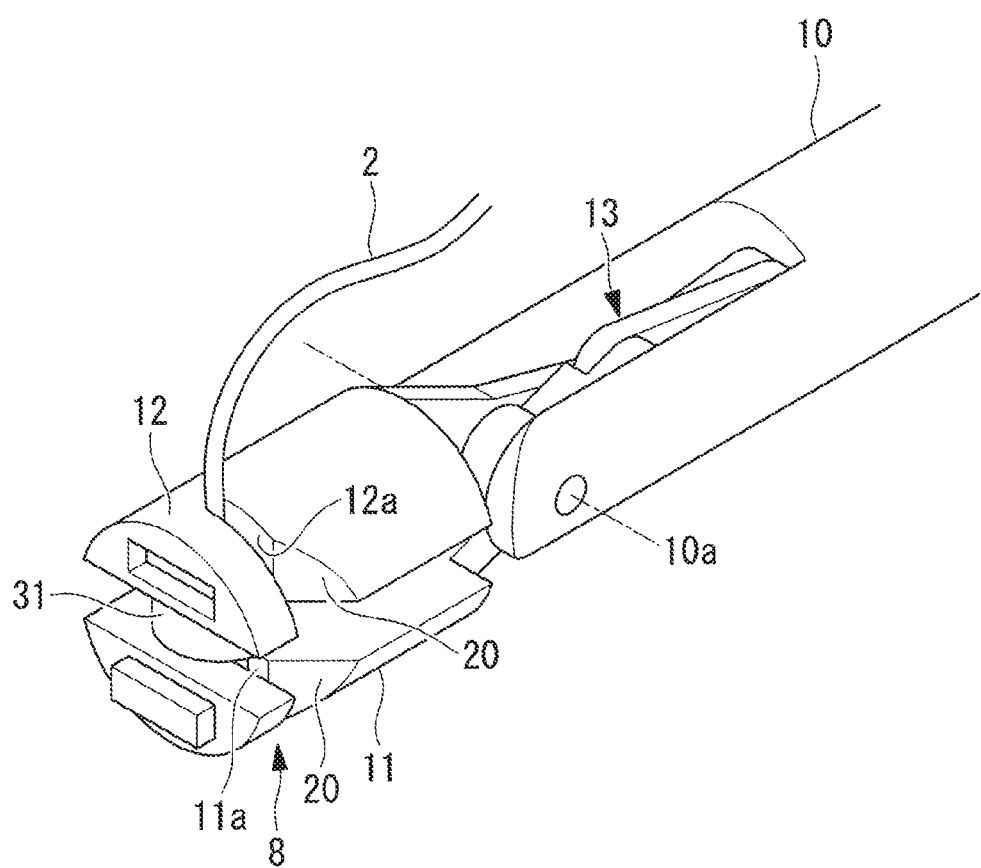
FIG. 2 is a perspective view showing a treatment portion of the suture device shown in FIG. 1.

As shown in FIG. 2, the treatment portion 8 includes: a base 10 fixed to the distal end of the elongated shaft member 7; and two gripping members 11, 12 which are provided at the base 10 in a pivotable manner about an axis (pivot) 10a orthogonal to a longitudinal axis of the elongated shaft member 7.

Figure 5:
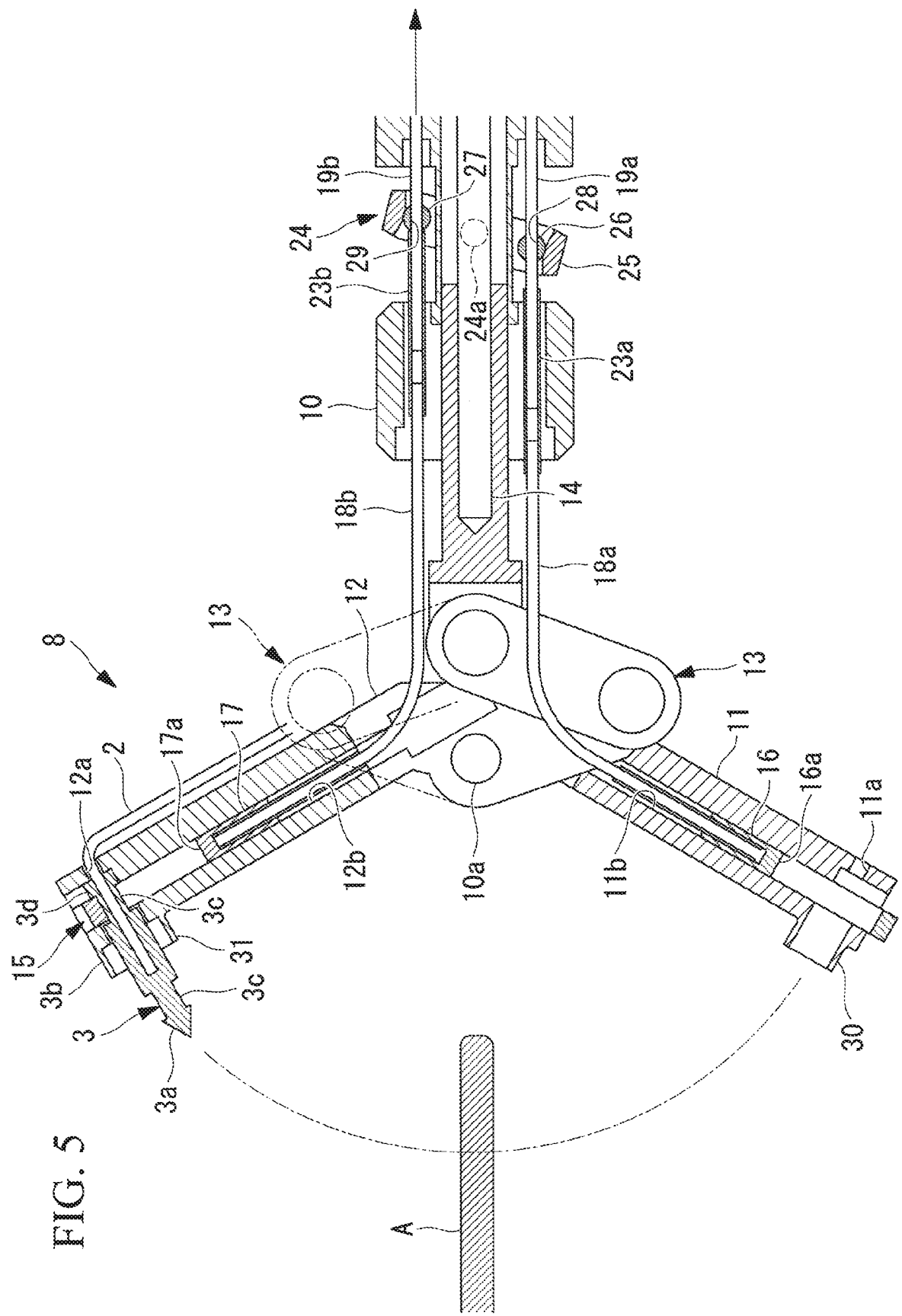
FIG. 5 is a longitudinal cross-sectional view showing a state where two gripping members of the treatment portion shown in FIG. 2 are opened.

As shown in FIG. 3, each of the two gripping members 11, 12 is connected to an opening-closing wire 14 via a link 13. With such a configuration, when the opening-closing wire 14 is pulled toward the proximal end side, as shown in FIGS. 2 and 3, both gripping members 11, 12 are disposed in a closed position where both gripping members 11, 12 extend approximately parallel along the longitudinal axis. On the other hand, when the opening-closing wire 14 is pushed out from the proximal end side toward the distal end side, as shown in FIG. 5, both gripping members 11, 12 are swung and disposed in an open position. In FIGS. 3, 5, 9 and 10, for the sake of simplification of illustration, the link 13 which is connected to one gripping member 11 is indicated by chain lines.

The two gripping members 11, 12 are provided with a passing mechanism 15 for passing the suture needle 3.

Here, the description is made with respect to the suture needle 3 which is used in the suture device 1 according to this embodiment.

As shown in FIGS. 3 to 4B, the suture needle 3 is formed in a substantially columnar shape. The suture needle 3 has the conical pointed end portion 3a on one end thereof, and the suture thread 2 is fixed to the other end of the suture needle 3 by adhesion or the like. On a center portion of the suture needle 3 in the longitudinal direction, a large-diameter portion 3b having a largest outer diameter size is formed with a predetermined length. Recessed portions 3c are formed on both sides of the large-diameter portion 3b in the longitudinal axis direction respectively at positions where the recessed portions 3c sandwich the large-diameter portion 3b. Each recessed portion 3c is recessed in the radial direction over the whole circumference. A flange portion 3d and a pointed end portion 3a are formed on the suture needle 3 at positions further toward the end portion sides of the suture needle 3 from the recessed portions 3c in the axial direction. The flange portion 3d and the pointed end portion 3a protrude more outside in the radial direction than the recessed portions 3c.

As shown in FIG. 3, the passing mechanism 15 is provided with: through holes (fitting hole portions) 11a, 12a formed in the two gripping members 11, 12 respectively at positions in the vicinity of pivotable distal end portions in a penetrating manner in the swing direction (opening-closing direction); holding members 16, 17 disposed in the respective gripping members 11, 12 in a movable manner in the longitudinal direction, which is orthogonal to the through holes 11a, 12a, along guide holes 11b, 12b formed along the longitudinal direction; and distal end wires 18a, 18b and drive wires 19a, 19b which drive the holding members 16, 17.

As shown in FIGS. 4A and 4B, the holding members 16, 17 are flat plate members which are made to translationally move in the longitudinal direction. The holding members 16, 17 have opening portions 16a, 17a which are open in the direction (sideward direction) intersecting with the moving direction so that the holding members 16, 17 are formed into a hook-shape as a whole. A plate thickness of the holding members 16, 17 is set smaller than a width size of the recessed portions 3c of the suture needle 3. The opening portions 16a, 17a of the holding members 16, 17 are formed with sizes which allow the flange portion 3d and the pointed end portion 3a to pass therethrough.

As shown in FIG. 3, the distal end wires 18a, 18b and the drive wires 19a, 19b are mutually connected to each other by connecting members 23a, 23b.

The distal end wires 18a, 18b have sufficiently higher rigidity than the drive wires 19a, 19b, thus allowing a transmission of both a tensile force and a compressive force.

The distal ends of the distal end wires 18a, 18b are fixed to the proximal end side of the holding members 16, 17, and proximal ends of the drive wires 19a, 19b are fixed to the manipulation portion 9 on the proximal end side of the elongated shaft member 7. When a tensile force is applied to the drive wires 19a, 19b by a manipulation of the manipulation portion 9, the tensile force is transmitted to the holding members 16, 17 through the connecting members 23a, 23b and the distal end wires 18a, 18b, and the holding members 16, 17 are pulled and moved toward the proximal end side.

The passing mechanism 15 also includes a swing member 24 arranged at a position further toward the proximal end side than the pivot 10a of the two gripping members 11, 12 such that the swing member 24 is swingable about a swing axis 24a orthogonal to the longitudinal axis of the elongated shaft member 7.

As shown in FIG. 3, the swing member 24 includes a ring-shaped member 25, and two columnar members 26, 27 disposed inside the ring-shaped member 25, and extending parallel to the axis 24a on both sides of the swing axis 24a with the axis 24a interposed therebetween. The respective columnar members 26, 27 are attached to the ring-shaped member 25 such that each of the columnar members 26, 27 is rotatable about a longitudinal axis of the columnar members 26, 27. Through holes 28, 29 which penetrate the columnar members 26, 27 in the diameter direction are formed in the columnar members 26, 27, and the drive wires 19a, 19b are made to pass through the through holes 28, 29.

Opening sizes of the through holes 28, 29 are set larger than the outer diameter size of the drive wires 19a, 19b, and are set smaller than the outer diameter size of the connecting members 23a, 23b. When a tensile force is applied to the drive wires 19a, 19b so that the drive wires 19a, 19b are moved toward the proximal end side, the connecting members 23a, 23b are not allowed to pass through the through holes 28, 29 and are caught on side surface of the columnar members 26, 27, and the columnar members 26, 27 are pulled toward the proximal end side of the elongated shaft member 7 so that the ring-shaped member 25 is made to swing about the swing axis 24a.

At this stage of manipulation, the columnar members 26, 27 are rotatable about the longitudinal axis of the columnar members 26, 27 so that a state is maintained where the through holes 28, 29 are extending along the longitudinal direction of the drive wires 19a, 19b.

As shown in FIG. 3, when one of the drive wires 19b pulls one of the columnar members 27 toward the proximal end side so that the swing member 24 is made to swing, the other columnar member 26 is pushed out toward the distal end side, and as a result, the connecting member 23a on the other drive wire 19a which passes through the through hole 28 of the pushed-out columnar member 26 is caught on the side surface of the columnar member 26 thus being pushed out toward the distal end side. When the connecting member 23a is pushed out, a compressive force in the direction of the other distal end wire 18a being pushed out toward the distal end side acts also on the other distal end wire 18a connected to the other drive wire 19a by the connecting member 23a. The distal end wire 18a has sufficiently high rigidity so that the distal end wire 18a transmits the compressive force without buckling whereby the holding member 16 at the distal end is pushed out toward the distal end side. Thereby, the holding and releasing of the suture needle 3 by two holding members 16, 17 can be switched alternatively.

The suture needle 3 is fitted in the through holes 11a, 12a of the gripping members 11, 12, and an end portion of the suture needle 3 passes through the opening portions 16a, 17a of the holding members 16, 17 so that the suture needle 3 is disposed in a position where the recessed portions 3c of the suture needle 3 match with the holding members 16, 17; in such a state, when the drive wires 19a, 19b are pulled so that the holding members 16, 17 are moved toward the proximal end side, inner edges of the opening portions 16a, 17a on the distal end side are inserted into the recessed portions 3c.

With such operations, since the flange portion 3d, the pointed end portion 3a and the large-diameter portion 3b are disposed in a position where the flange portion 3d and the large-diameter portion 3b sandwich the recessed portions 3c therebetween and the pointed end portion 3a and the large-diameter portion 3b sandwich the recessed portions 3c therebetween, the flange portion 3d or the pointed end portion 3a and the large-diameter portion 3b engage with the holding member 16 or the holding member 17 in the longitudinal direction of the suture needle 3 so that the suture needle 3 is engaged so as not to move in the longitudinal direction in the through holes 11a, 12a. Further, inner edges of the holding members 16, 17 push the recessed portions 3c in the radial direction due to tension applied to the holding members 16, 17 and hence, the suture needle 3 is pressed against the inner surfaces of the through holes 11a, 12a thus being more firmly fixed due to the friction generated between the suture needle 3 and the inner surfaces of the through holes 11a, 12a.

As shown in FIG. 2, a notch 20 is formed on each of the gripping members 11, 12 at a position (side position) which corresponds to the opening portions 16a, 17a of the holding members 16, 17 so as to penetrate the gripping members 11, 12 from outer surfaces of the gripping members 11, 12 to the through holes 11a, 12a. The minimum width of the notches 20 is set larger than the diameter size of the suture thread 2 so that the suture thread 2 can be moved in and out of the through holes 11a, 12a through the notches 20. The notches 20 have a shape which is gradually opened toward the outer surface of the gripping members 11, 12, thus facilitating the movement of the suture thread 2 in and out of the through holes 11a, 12a.

Further, the suture device 1 according to this embodiment includes a first cylindrical portion (tubular portion) 30 and a second cylindrical portion (tubular portion) 31 which are formed on the gripping members 11, 12 respectively. The first cylindrical portion 30 extends in the axial direction of the through hole 11a into which the pointed end portion 3a side of the suture needle 3 is inserted from a surface of the other gripping member 11 which opposedly facing one of the gripping members 12. The second cylindrical portion 31 extends in the axial direction of the through hole 12a from a surface of the one of the gripping members 12 which opposedly facing the other gripping member 11. The first cylindrical portion 30 and the second cylindrical portion 31 form a contact portion which suppresses the movement of the tissue A in the direction along a surface of the tissue A.

The first cylindrical portion 30 is disposed in a position where the first cylindrical portion 30 surrounds substantially the whole circumference of the through hole 11a. The second cylindrical portion 31 is disposed in a position where the second cylindrical portion 31 surrounds substantially the whole circumference of the through hole 12a.

The term "substantially the whole circumference" is used in the description here because the gripping members 11, 12 are cut due to the formation of the notches 20 and hence, each of the first cylindrical portion 30 and the second cylindrical portion 31 is also partially cut in the circumferential direction corresponding to the notches 20.

The second cylindrical portion 31 is formed with an inner diameter size larger than an outer diameter size of the first cylindrical portion 30.

As shown in FIG. 3, in a state where the two gripping members 11, 12 are most closed, the first cylindrical portion 30 and the second cylindrical portion 31 are coaxially disposed with a gap therebetween in the radial direction and, at the same time, are disposed such that a distal end portion of the first cylindrical portion 30 and a distal end portion of the second cylindrical portion 31 partially overlap with each other in the axial direction.

As shown in FIG. 1, the manipulation portion 9 is disposed on the proximal end side of the elongated shaft member 7, and includes an opening-closing manipulation portion 21 for performing an opening-closing action of the two gripping members 11, 12; and a passing manipulation portion 22 for pulling the two drive wires 19a, 19b. The opening-closing manipulation portion 21 includes a handle 21a formed in the shape of scissor handles, and the opening-closing wire 14 is pushed and pulled in the longitudinal axis direction by an opening-closing manipulation of the handle 21a.

The operation of the suture device 1 according to this embodiment having such a configuration are described hereinafter.

In suturing a tissue (suture object) A inside the body using the suture device 1 according to this embodiment, first, the insertion portion 5 of the endoscope 4 is inserted into the body and, while the inside of the body is observed using the observation optical system 5c arranged at a distal end of the insertion portion 5, the distal end of the insertion portion 5 is disposed at a position where a portion to be sutured falls within the visual field range of the endoscope 4.

Meanwhile, with respect to the suture device 1, the handle 21a of the opening-closing manipulation portion 21 is manipulated so as to close the two gripping members 11, 12 of the treatment portion 8 as shown in FIG. 3, and the suture needle 3 is disposed such that the suture needle 3 passes through the through holes 11a, 12a of the two gripping members 11, 12 which are aligned in one row. Further, with a manipulation of a handle 22a of the passing manipulation portion 22, a tensile force is applied to the other drive wire 19b which pulls the holding member 17 on the flange portion 3d side of the suture needle 3 toward the proximal end side.

With such operations, the tensile force is transmitted to the distal end wire 18b connected to the drive wire 19b so that the holding member 17 is pulled toward the proximal end side, while the connecting member 23b which connects the drive wire 19b and the distal end wire 18b with each other abuts against the side surface of the other columnar member 27 of the swing member 24. As a result, the tensile force of the drive wire 19b is applied to the other columnar member 27 and that the columnar member 27 is pulled toward the proximal end side, so that the swing member 24 is made to swing about the swing axis 24a at such a position thus pushing out one of the columnar members 26 toward the distal end side.

With such operations, the tensile force applied to the other drive wire 19b is transmitted to the other holding member 17 via the connecting member 23b and the other distal end wire 18b so that the holding member 17 is moved toward the proximal end side, whereby the holding member 17 is inserted into the recessed portion 3c on the flange portion 3d side of the suture needle 3. Together with such operations, the connecting member 23a mounted on one of the drive wires 19a is pushed out toward the distal end side by the side surface of the columnar member 26 so that the holding member 16 is moved toward the distal end side and is brought into a state of releasing the suture needle 3 on the pointed end portion 3a side.

In such a state, the suture device 1 according to this embodiment is inserted into the channel 5b from the treatment portion 8 side through an insertion port arranged on the proximal end side of the insertion portion 5 disposed outside the body, and the treatment portion 8 is made to project from the distal end surface of the insertion portion 5. With such operations, the treatment portion 8 is also disposed within the visual field range of the observation optical system 5c of the endoscope 4.

Figure 11A:
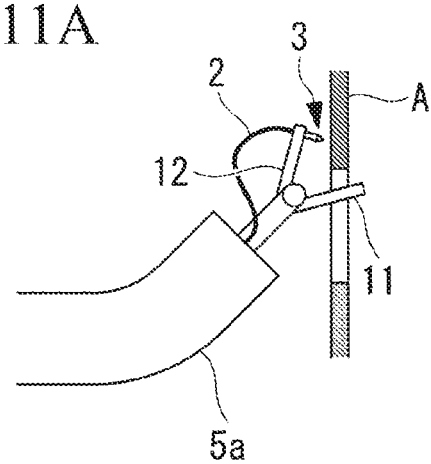
FIG. 11A is a view for describing a tissue suturing action performed by the suture device according to the embodiment.

Then, the tissue A which is a portion to be sutured is disposed in front of the treatment portion 8 while an endoscope image is observed; with a manipulation of the handle 21a of the opening-closing manipulation portion 21, the opening-closing wire 14 is pushed toward the distal end side so that the two gripping members 11, 12 are made to swing via the links 13 as shown in FIGS. 5 and 11A so as to dispose the two gripping members 11, 12 in mutually opened positions. The holding member 16 on the pointed end portion 3a side is in a released state of the suture needle 3, and the holding member 17 on the flange portion 3d side is in a fixed state of the suture needle 3 to the gripping member 12 and hence, the two gripping members 11, 12 are opened in a state where the pointed end portion 3a of the suture needle 3 projects toward the inside.

Next, the treatment portion 8 is made to advance to a position where the tissue A is sandwiched between the two gripping members 11, 12, and then, with a manipulation of the opening-closing manipulation portion 21, the opening-closing wire 14 is drawn back toward the proximal end side so as to close the two gripping members 11, 12 via the links 13.

Figure 6:
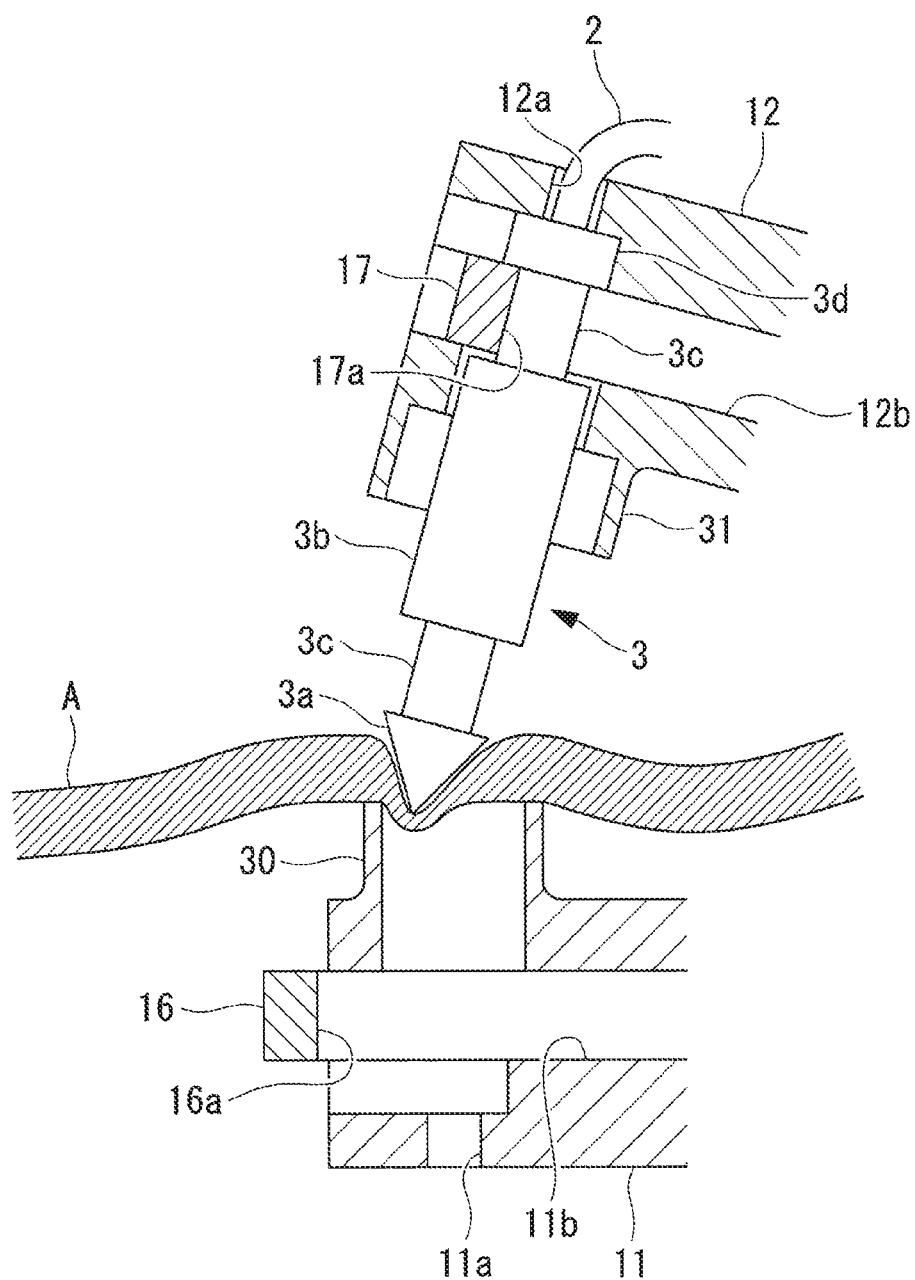
FIG. 6 is a longitudinal cross-sectional view showing a state where a pointed end of the suture needle is brought into contact with tissue due to a swinging of the gripping members of the suture device shown in FIG. 2.

When the pair of gripping members 11, 12 is moved to close relative to each other, as shown in FIG. 6, first, the pointed end portion 3a of the suture needle 3 is brought into contact with the tissue A. When the pair of gripping members 11, 12 are further closed, in the case where the tissue A is soft tissue or the like, as shown in FIG. 7, a portion of the tissue A pressed by the pointed end portion 3a of the suture needle 3 is pushed into the through hole 11a of one gripping member 11.

In such a case, according to the suture device 1 of this embodiment, in the course of the closing action shown in FIG. 6, the first cylindrical portion 30 and the second cylindrical portion 31 are brought into contact with front and back surfaces of the tissue A and sandwich the tissue A.

When the pair of gripping members 11, 12 are made to swing in the direction of further closing, a distal end of the first cylindrical portion 30 and a distal end of the second cylindrical portion 31 are gradually firmly pressed against the front and back surfaces of the tissue A so that the movement of the tissue A is restricted by friction.

Figure 7:
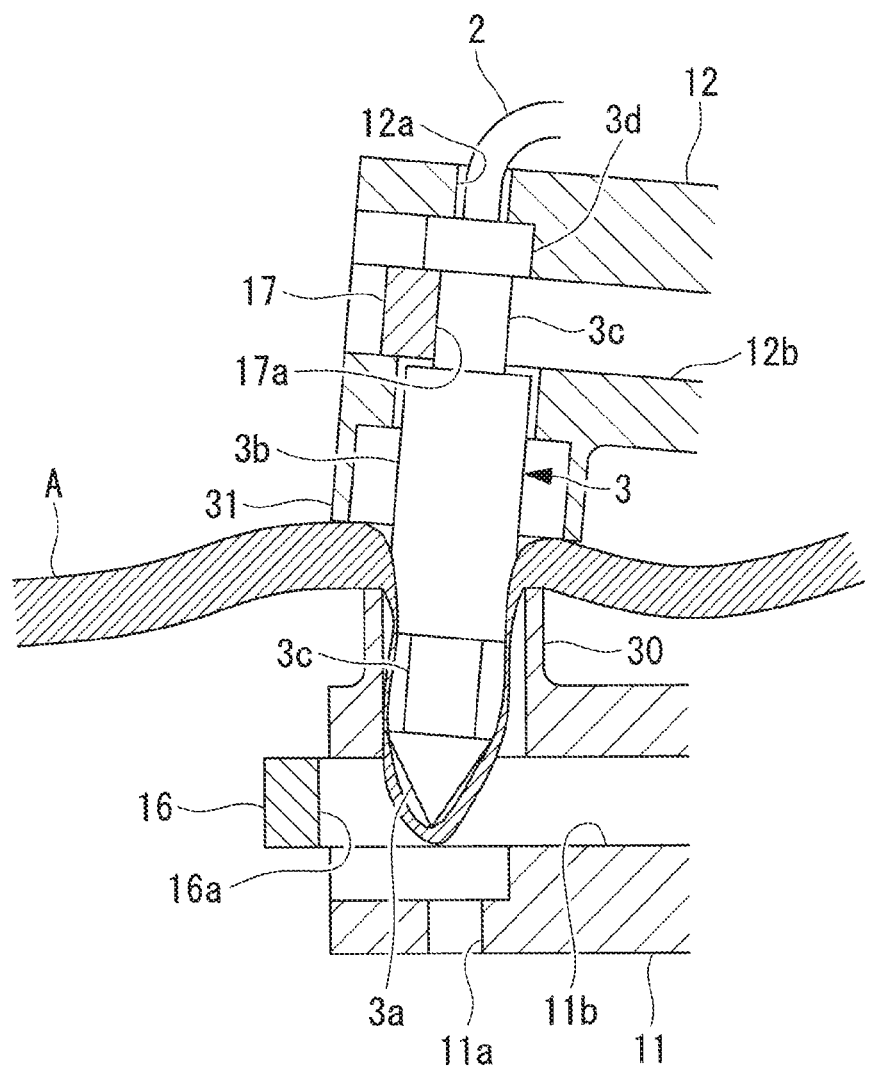
FIG. 7 is a longitudinal cross-sectional view showing a state where the gripping members are made to further swing in the closing direction from the state shown in FIG. 6 so that the tissue is pushed into a through hole.
Figure 8:
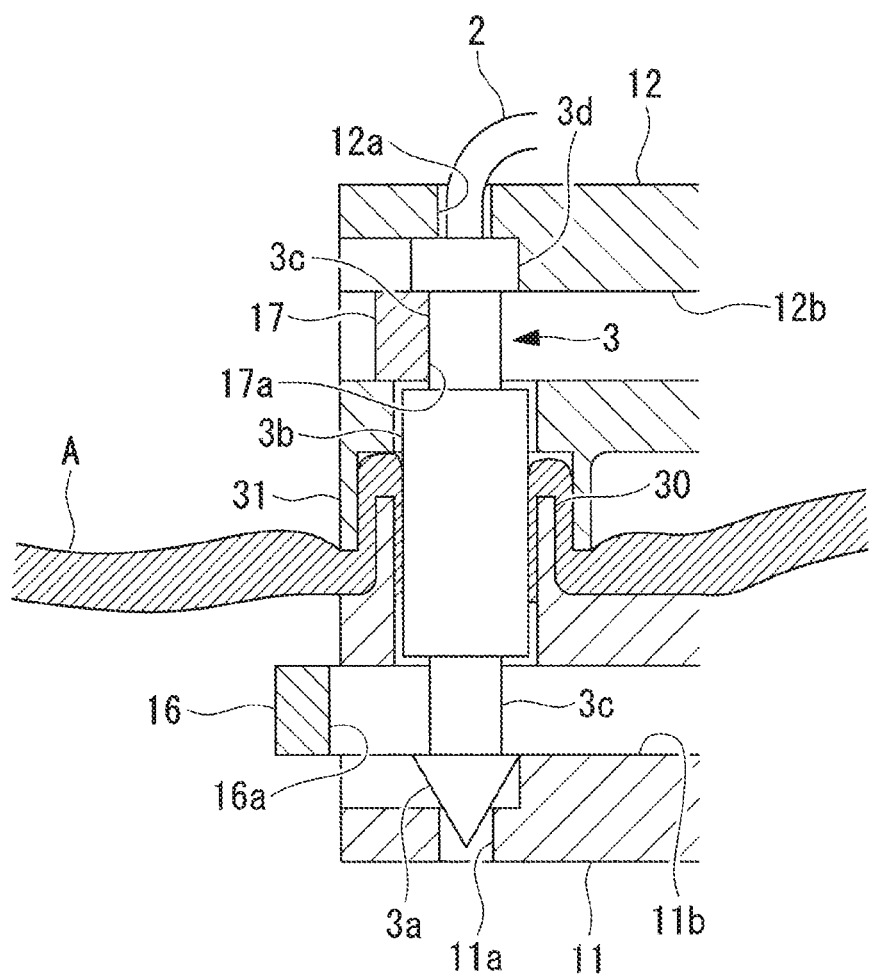
FIG. 8 is a longitudinal cross-sectional view showing a state where the gripping members are made to further swing in the closing direction from the state shown in FIG. 7 so that the suture needle penetrates the tissue.

Accordingly, thereafter, as shown in FIG. 7, when the pair of gripping members 11, 12 are moved so as to be completely closed so that the suture needle 3 is further pressed against the tissue A, a tension on the tissue A inside the through hole 11a is increased and hence, as shown in FIG. 8, the tissue A is easily pierced by the pointed end portion 3a of the suture needle 3. When the tissue A to which the tension is applied is pierced by the pointed end portion 3a of the suture needle 3, the tissue A contracts so as to return to its natural shape due to elasticity.

Figure 9:
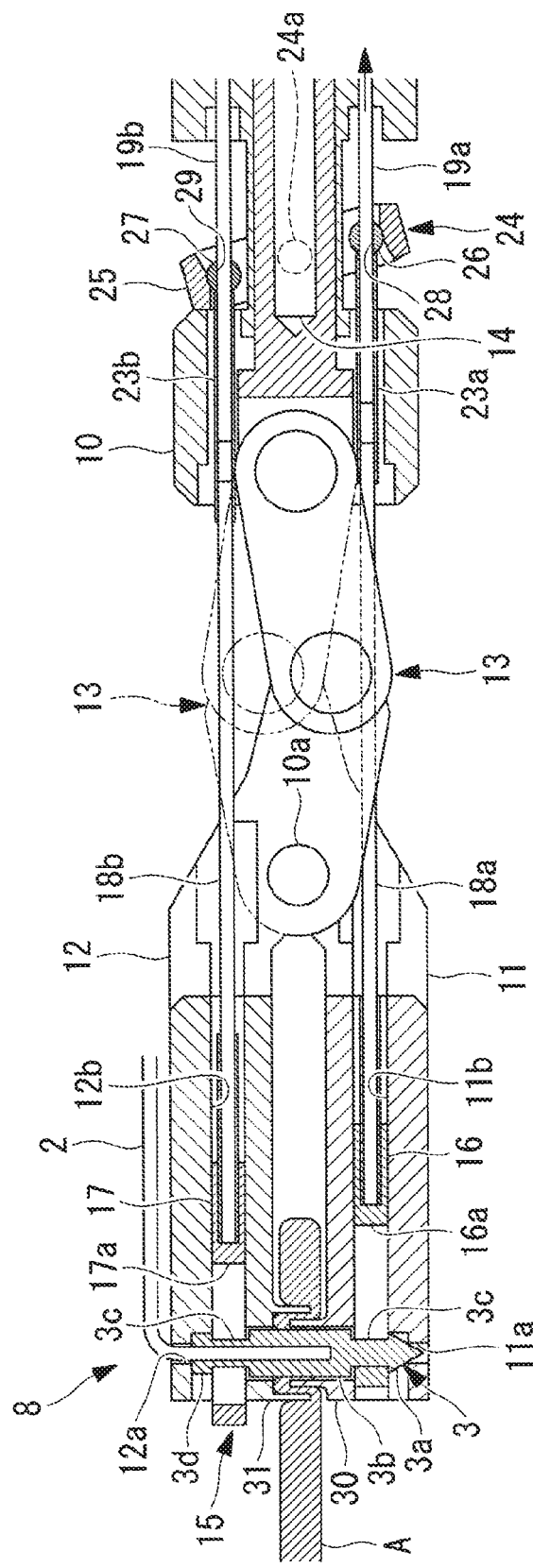
FIG. 9 is a longitudinal cross-sectional view showing a state where the two gripping members are closed from the state shown in FIG. 8 so that the suture needle penetrates the tissue, and the holding of the suture needle by the holding members is switched.

As a result, as shown in FIG. 9, the pointed end portion 3a of the suture needle 3 punctures the tissue A from one side, and is inserted into the through hole 11a of the other gripping member 11 disposed on the other side of the tissue A so that the tissue A is sandwiched between the two gripping members 11, 12.

In this case, the first cylindrical portion 30 and the second cylindrical portion 31 are disposed in a position where the first cylindrical portion 30 and the second cylindrical portion 31 overlap with each other in the axial direction, and both cylindrical portions are disposed with a gap therebetween in the radial direction so that the tissue A sandwiched between both cylindrical portions is maintained in a fine state without being crushed.

Figure 11B:
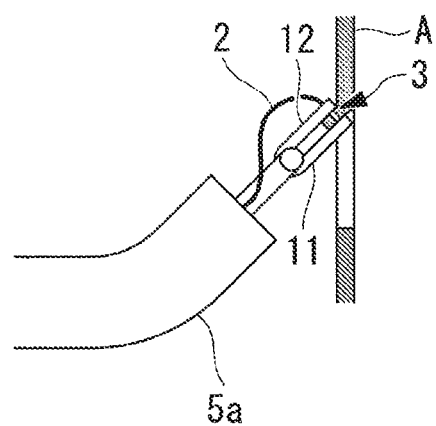
FIG. 11B is a view for describing the tissue suturing action performed by the suture device according to the embodiment.

In such a state, the handle 22a of the passing manipulation portion 22 is manipulated so as to apply a tensile force to the drive wire 19a which pulls the holding member 16 on the pointed end portion 3a side; the tensile force is transmitted to the drive wire 19a from the handle 22a so that the holding member 16 on the pointed end portion 3a side is pulled, whereby the holding member 16 is inserted into the recessed portion 3c on the pointed end portion 3a side as shown in FIGS. 9 and 11B. At this time, the punctured tissue A contracts to a position where the tissue A does not interfere with the holding member 16 and hence, the tissue A will not be sandwiched between the holding member 16 and the suture needle 3. Meanwhile, with swinging of the swing member 24, the holding member 17 on the flange portion 3d side is made to advance to release the suture needle 3.

Figure 10:
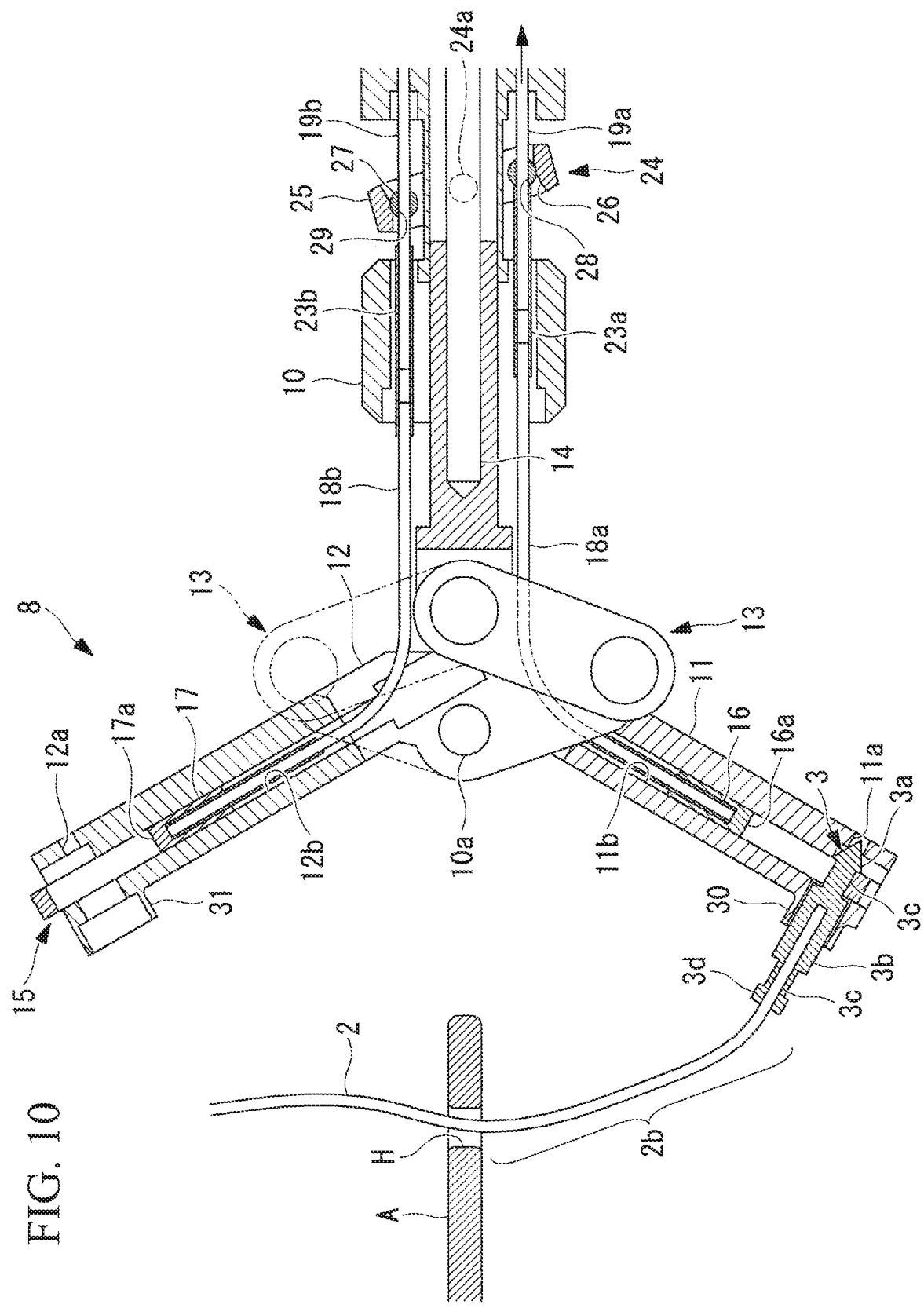
FIG. 10 is a longitudinal cross-sectional view showing a state where the two gripping members are opened again from the state shown in FIG. 9.
Figure 11C:
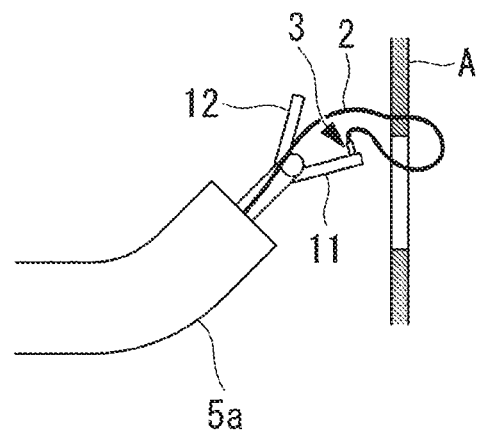
FIG. 11C is a view for describing the tissue suturing action performed by the suture device according to the embodiment.

Then, the handle 21a of the opening-closing manipulation portion 21 is manipulated again so as to push the opening-closing wire 14 toward the distal end side to open the two gripping members 11, 12 via the links 13. The holding member 17 on the flange portion 3d side has released the suture needle 3, and the holding member 16 on the pointed end portion 3a side fixes the suture needle 3 to the gripping member 11, whereby, as shown in FIGS. 10 and 11C, the two gripping members 11, 12 are opened in a state where the suture needle 3 projects with the flange portion 3d side of the suture needle 3 pointing toward the inside.

Figure 11D:
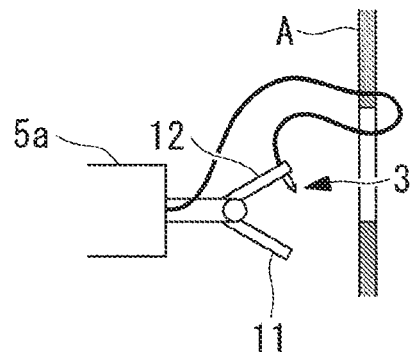
FIG. 11D is a view for describing the tissue suturing action performed by the suture device according to the embodiment.

As a result, the suture needle 3 passes through a hole H formed in the tissue A so that the suture thread 2 is made to penetrate the tissue A through the hole H. In such a state, the suture needle 3 is held by the gripping member 11 with the flange portion 3d side being made to project, whereby a portion 2b of the suture thread 2 between the tissue A and the flange portion 3d is inserted into the through hole 12a of the gripping member 12 via the notch 20, and then the two gripping members 11, 12 are opened-closed (blank shot) at a position where the gripping members 11, 12 do not sandwich the tissue A so that the suture needle 3 is passed to one of the gripping members 12 by the passing mechanism 15. With such operations, as shown in FIG. 11D, the suture needle 3 can be held by the gripping member 12 again in a state where the pointed end portion 3a side is made to project.

Figure 11E:
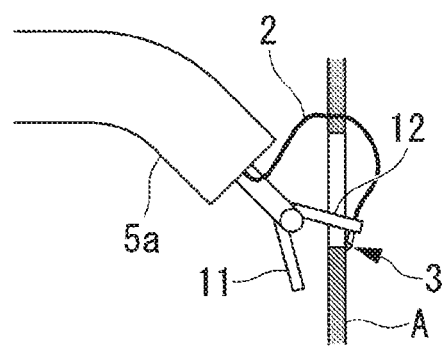
FIG. 11E is a view for describing the tissue suturing action performed by the suture device according to the embodiment.
Figure 11F:
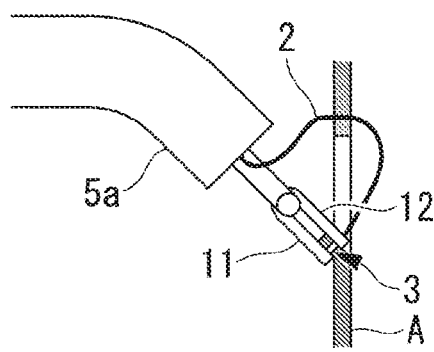
FIG. 11F is a view for describing the tissue suturing action performed by the suture device according to the embodiment.
Figure 11G:
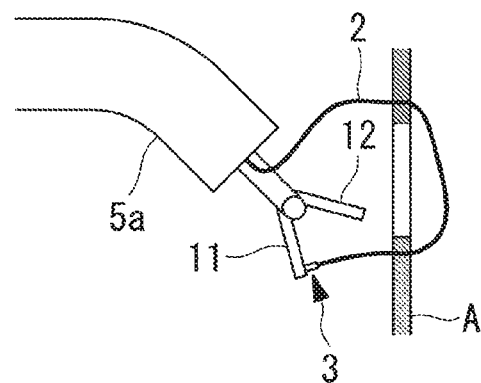
FIG. 11G is a view for describing the tissue suturing action performed by the suture device according to the embodiment.

Then, as shown in FIGS. 11E, 11F and 11G, a place where the suture thread 2 is made to penetrate the tissue A is changed, and the procedure described above is repeated so that the suture thread 2 can be made to penetrate the tissue A at two or more places as shown in FIG. 11G. Thereafter, the suture thread 2 is pulled so that the tissue A can be sutured in a tightly closed state.

As described above, according to the suture device 1 of this embodiment, in puncturing the tissue A by the suture needle 3, a tension of the tissue A in a region where the pointed end portion 3a is in contact with the tissue A is increased and hence, even when the tissue A is a soft tissue or the like which is easily stretched, the tissue A can be more reliably pierced so that jamming of the tissue A by the gripping members 11, 12 can be prevented. This has the advantageous effect that a suturing operation can be performed smoothly.

Figure 12A:
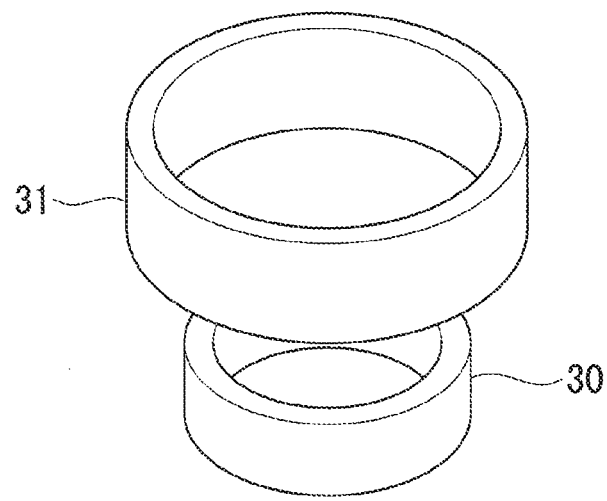
FIG. 12A is a perspective view showing a relationship between a tubular portion and a projection portion provided on the gripping members of the treatment portion shown in FIG. 2 respectively.

In this embodiment, the first cylindrical portion 30 and the second cylindrical portion 31 shown in FIG. 12A are adopted as the tubular portion and the projection portion formed on the pair of gripping members 11, 12, but the invention is not limited to this configuration, and the tubular portion and the projection portion may be formed in any arbitrary tubular shape including a polygonal tubular shape such as a quadrangular tubular shape.

Figure 12B:
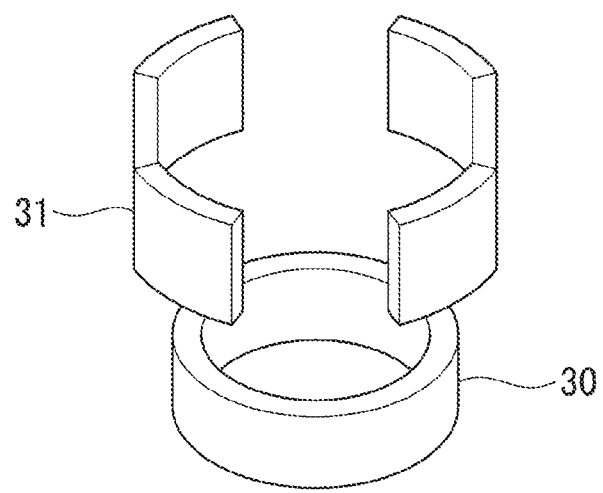
FIG. 12B is a perspective view of a modification of the tubular portion and the projection portion shown in FIG. 12A.

Furthermore, as shown in FIG. 12B, the second cylindrical portion 31 may be configured such that the second cylindrical portion 31 is divided in the circumferential direction, and presses the tissue A at two or more places (four places in the drawing) in the circumferential direction. A shape of the second cylindrical portion 31 may be an arcuate plate shape as shown in FIG. 12B or another shape such as a rod shape. Also in this case, the second cylindrical portion 31 is required to be disposed so as to press the tissue A at a position outside the first cylindrical portion 30 in the radial direction, with a gap between the second cylindrical portion 31 and the first cylindrical portion 30.

With such a configuration, a tension can be applied to the tissue A between the cylindrical portions 30, 31 by a pair of second cylindrical portions 31 disposed on both sides of the first cylindrical portion 30 with the first cylindrical portion 30 being interposed between the pair of second cylindrical portions 31 so that the tissue A in the first cylindrical portion 30 can be easily pierced by the pointed end portion 3a.

Figure 13A:
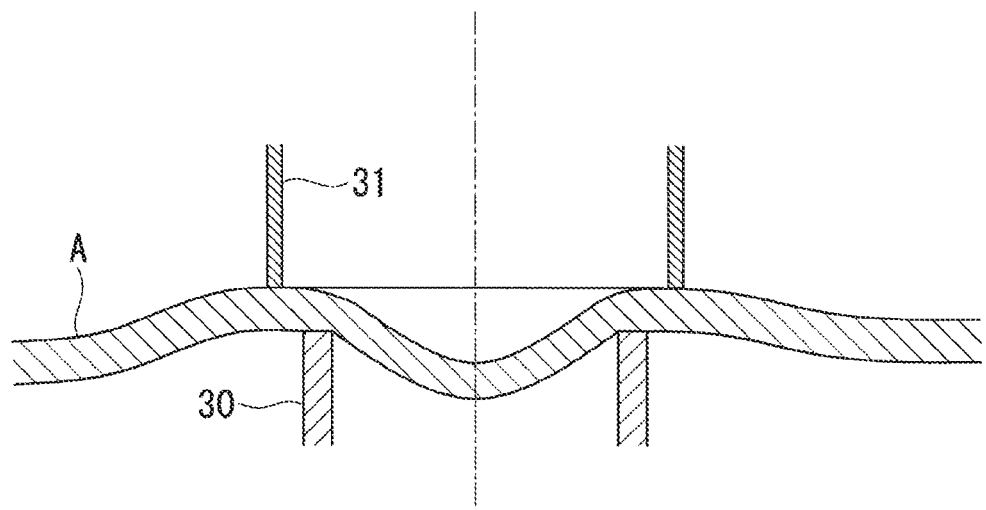
FIG. 13A is a longitudinal cross-sectional view showing a state of the projection portion in the modification which is provided on the gripping member of the treatment portion shown in FIG. 2 before the projection portion is deformed.
Figure 13B:
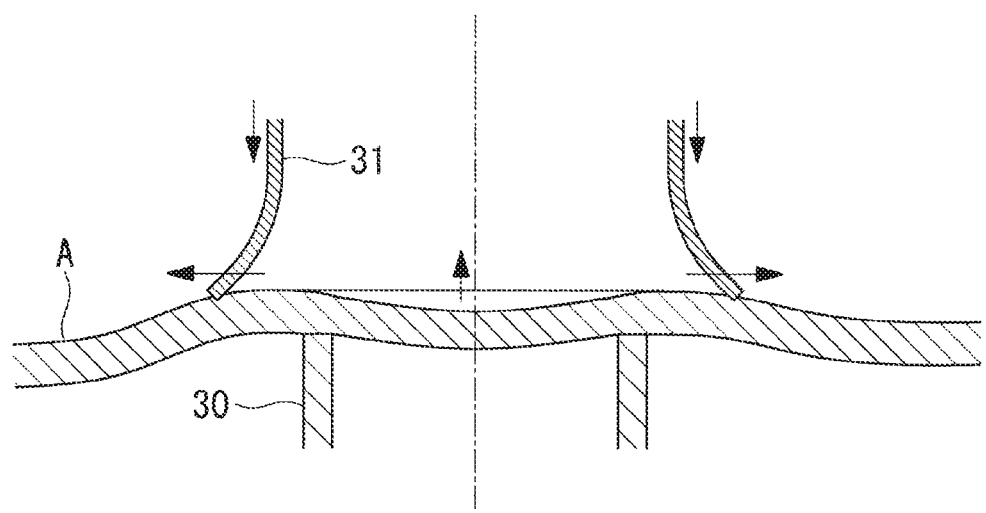
FIG. 13B is a longitudinal cross-sectional view showing a state of the projection portion shown in FIG. 13A after the projection portion is deformed.

The second cylindrical portion 31 may be formed of an elastic member which can be elastically deformed by pressing the tissue A. With such a configuration, a load applied to the tissue A can be reduced. It is particularly desirable to adopt the second cylindrical portion 31 having a configuration as shown in FIG. 13A, that is, the second cylindrical portion 31 is formed of an elastic member which is bent such that a ends of the tissue A spreads outward in the radial direction when a distal end of the second cylindrical portion 31 is further pressed against the tissue A as shown in FIG. 13B from a position where the distal end of the second cylindrical portion 31 is in contact with the tissue A.

With such a configuration, as the second cylindrical portion 31 is pressed against the tissue A, a frictional force toward the radially outward direction acts so as to increase a tension applied to the tissue A between the cylindrical portions 30, 31 so that a tension can be applied to the tissue A more effectively.

In this embodiment, the configuration is adopted where when the pair of gripping members 11, 12 are disposed in a most closed position, the first cylindrical portion 30 and the second cylindrical portion 31 overlap with each other in the axial direction, but an overlap amount thereof may be arbitrarily determined according to a thickness of the tissue A to be sutured. When the tissue A has a large thickness, an overlap amount may be set to a small value or may be set to zero.

From the above-described embodiments, the following aspects of the present invention are derived.

According to one aspect of the present invention, there is provided a suture device which includes: an elongated shaft member extending along a longitudinal axis; a pair of two gripping members, the gripping members being provided at a distal end of the elongated shaft member in a pivotable manner about a pivot orthogonal to the longitudinal axis so as to be opened and closed relative to each other; and a passing mechanism configured to pass a suture needle between the gripping members, the suture needle to which a suture thread is attached and which has a pointed end portion, wherein each of the gripping members includes: a fitting hole portions which is formed along an opening and closing direction of the gripping members, and to which the suture needle is detachably fitted; and a contact portion which is brought into contact with either of front and back surfaces of a suture object in a course of a closing action of the pair of the gripping members so as to suppress a movement of the suture object in a direction along the surface of the suture object.

According to this aspect, the fitting hole portion of one gripping member holds the suture needle in a fitted state with the pointed end portion of the suture needle toward the other gripping member side. When both gripping members are closed so as to grip a suture object therebetween, the suture needle penetrates the suture object, and is fitted into the fitting hole of the other gripping member. In such a state, the passing mechanism releases the holding of the suture needle by one of the gripping members and holds the suture needle by the other gripping member. Then, by opening both gripping members, the suture needle is passed from one of the gripping members to the other gripping member so that the suture thread attached to the suture needle can be made to penetrate the suture object.

In this case, when the pair of gripping members is moved to close relative to each other, in the course of such a closing action, the pointed end portion of the suture needle is brought into contact with and pushes the suture object. At the same time, the each of the contact portion is brought into contact with the either of the front and back surface of the suture object so as to suppress a movement of the suture object by friction. In such a state, when the pair of gripping members are further closed, the pointed end portion of the suture needle further pushes the suture object. The movement of the suture object is suppressed by the contact portions and hence, a tension of the suture object in a region where the pointed end portion of the suture needle is in contact with the suture object is increased, and thus the suture object is easily pierced by the pointed end portion. As a result, the suture needle can be made to ensure penetrating the suture object so that jamming of the suture object by the passing mechanism can be prevented. Accordingly, a suturing operation can be performed smoothly.

In the above-mentioned aspect, the contact portions may include: a tubular portion formed so that the tubular portion surrounds a periphery of the fitting hole portion of one of the gripping members provided with the fitting hole portion into which the pointed end portion is inserted and that the tubular portion extends towards the other of the gripping members; and a projection portion, formed at a position where the projection portion surrounds the periphery of the fitting hole portion of the other of the gripping members, and extending toward one of the gripping members, and the tubular portion and the projection portion may be formed such that the tubular portion and the projection portion are arranged at positions spaced from each other in a radial direction of the fitting hole portions when the two gripping members are completely closed.

With such a configuration, when the pair of gripping members is moved to close relative to each other, in the course of such a closing action, the pointed end portion of the suture needle is brought into contact with and pushes the suture object. At the same time, the tubular portion formed on one gripping member facing the pointed end portion is brought into contact with the back surface of the suture object, and the projection portion formed on the other gripping member is brought into contact with the front surface of the suture object. With such a configuration, the back surface of the suture object is pressed against the distal end of the tubular portion over the whole circumference and, at the same time, the suture object is pressed by the projection portion from the front surface side at the outer side of the tubular portion in the radial direction.

Accordingly, the tip of the suture needle is pressed against the suture object which is stretched due to tension. As a result, the suture needle can be made to ensure penetrating the suture object and hence, a suturing operation can be performed smoothly.

When the two gripping members are completely closed, the tubular portion and the projection portion are disposed at positions away from each other in the radial direction. Accordingly, it is possible to prevent the suture object sandwiched between both the tubular portion and the projection portion from being crushed and damaged.

In the above-mentioned aspect, the tubular portion may be formed into a cylindrical shape, and the projection portion may be formed into a cylindrical shape having an inner diameter larger than an outer diameter of the tubular portion.

With such a configuration, the back surface of the suture object is pressed against the distal end of the cylindrical tubular portion over substantially the whole circumference. At the same time, the suture object is pressed by the cylindrical projection portion over substantially the whole circumference from the front surface side on the radially outer side of the tubular portion. Accordingly, the tip of the suture needle is pressed against the suture object which is stretched like a drumhead due to tension. As a result, the suture needle can be made to ensure penetrating the suture object and hence, a suturing operation can be performed smoothly.

In the above-mentioned aspect, the projection portion may be formed of two or more projection portions which are arranged at intervals in a circumferential direction of the fitting hole portion.

With such a configuration, the back surface of the suture object is pressed against the distal end of the cylindrical tubular portion over substantially the whole circumference. At the same time, a tension is applied to the suture object from the front surface side in one or more directions by two or more projection portions on the radially outer side of the tubular portion. Accordingly, the tip of the suture needle is pressed against the suture object which is stretched due to tension. As a result, the suture needle can be made to ensure penetrating the suture object and hence, a suturing operation can be performed smoothly.

In the above-mentioned aspect, the projection portion may be formed of an elastic member which is elastically deformed in contact with the suture object.

With such a configuration, when the projection portion is pressed against the front surface of the suture object, the projection portion formed of an elastic member is elastically deformed so that a pressing force is reduced. Accordingly, it is possible to prevent an excessively large pressing force from being applied to the suture object.

In the above-mentioned aspect, the projection portion may be elastically deformed such that a distal end of the projection portion is moved in a radially outward direction.

With such a configuration, as one gripping member is closed, the projection portion formed of an elastic member is brought into contact with the front surface of the suture object at the radially outer side of the tubular portion which is in contact with the back surface side of the suture object, thus being elastically deformed such that the distal end of the projection portion is moved toward the outer side in the radial direction. Accordingly, a tension applied to the suture object arranged inside the tubular portion is increased. As a result, the suture needle can be made to ensure penetrating the suture object and hence, a suturing operation can be performed smoothly.

According to the aforementioned aspects, it is possible to acquire an advantageous effect that the suture needle is made to ensure penetrating the suture object so that a suturing operation can be performed smoothly.

REFERENCE SIGNS LIST 1 suture device
2 suture thread
3 suture needle
3a pointed end portion
7 elongated shaft member
10a pivot
11, 12 gripping member
11a, 12a through hole (fitting hole portion)
15 passing mechanism
30 first cylindrical portion (contact portion, tubular portion)
31 second cylindrical portion (contact portion, projection portion, elastic member)
A tissue (suture object)

The invention claimed is:

1. A suture device comprising:
an elongated shaft extending along a longitudinal axis;
a first jaw and a second jaw provided at a distal end of the elongated shaft in a pivotable manner about a pivot orthogonal to the longitudinal axis so as to be opened and closed relative to each other; and
a suture needle having a first end for attachment of a suture thread and a second end having a pointed end, wherein the first end of the suture needle is attached to the second jaw;
the first jaw includes a tube for accepting the second end of the suture needle when the first jaw and the second jaw are closed,
the second jaw includes a projection extending in a direction from the first end of the suture needle attached to the second jaw toward the second end of the suture needle, the projection being formed at a position where the projection surrounds the tube in a state where the first jaw and the second jaw are closed,
the tube and the projection are configured to be brought into contact with front and back surfaces of a suture object in the state where the first jaw and the second jaw are closed to capture a portion of the suture object;
the tube is formed into a cylindrical shape, and the projection is formed into a cylindrical shape having an inner diameter larger than an outer diameter of the tube such that a gap is formed between the inner diameter of the projection and the outer diameter of the tube and the portion of the suture object is captured in the gap to suppress a movement of the suture object relative to the suture needle; and
the projection is formed of an elastic member which is elastically deformed in contact with the suture object.

2. The suture device according to claim 1, wherein the projection is elastically deformed such that a distal end of the projection is moved in a radially outward direction.

3. The suture device according to claim 1, further comprising a passing mechanism configured to pass the suture needle from being disposed in the second jaw to being disposed in the first jaw.

* * * * *